(12) United States Patent
Kegelman et al.

(10) Patent No.: US 8,066,943 B2
(45) Date of Patent: Nov. 29, 2011

(54) CLINICAL ANALYZER HAVING A VARIABLE CYCLE TIME AND THROUGHPUT

(75) Inventors: Joseph E. Kegelman, Wilmington, DE (US); Kevin J. Clair, Middletown, DE (US); Jeffrey K. Parmer, Newark, DE (US); Richard G. Brodeur, Newark, DE (US); Alexander V. Evers, Wilmington, DE (US); Mark R. Lloyd, Elkton, MD (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 377 days.

(21) Appl. No.: 11/941,204

(22) Filed: Nov. 16, 2007

(65) Prior Publication Data

US 2009/0129979 A1 May 21, 2009

(51) Int. Cl.
*G01N 21/00* (2006.01)
*G01N 31/00* (2006.01)
*G01N 33/00* (2006.01)
*G01N 35/00* (2006.01)
*G01N 35/02* (2006.01)

(52) U.S. Cl. ............... 422/67; 422/63; 422/65; 436/43; 436/50

(58) Field of Classification Search .................. None
See application file for complete search history.

(56) References Cited

U.S. PATENT DOCUMENTS

| | | | |
|---|---|---|---|
| 4,774,055 A * | 9/1988 | Wakatake et al. ............... 422/64 |
| 5,252,612 A | 10/1993 | Arison et al. | |
| 5,576,215 A | 11/1996 | Burns et al. | |
| 5,846,491 A | 12/1998 | Choperena et al. | |
| 5,985,672 A | 11/1999 | Kegelman et al. | |
| 6,096,561 A * | 8/2000 | Tayi .................................. 422/63 |
| 6,284,472 B1 | 9/2001 | Wei et al. | |
| 6,723,288 B2 | 4/2004 | Devlin, Sr. et al. | |
| 7,015,042 B2 | 3/2006 | Devlin, Sr. | |
| 7,169,356 B2 | 1/2007 | Gebrian et al. | |
| 7,390,458 B2 * | 6/2008 | Burow et al. ..................... 422/63 |
| 2006/0051243 A1 | 3/2006 | Chow et al. | |

* cited by examiner

*Primary Examiner* — Jill Warden
*Assistant Examiner* — Charles D Hammond
(74) *Attorney, Agent, or Firm* — Leland K. Jordan (57) ABSTRACT

A clinical analyzer having the capability to operate at both a higher and lower throughput, depending upon the assay load demand experienced by the hospital or laboratory, so that analyzer throughput most closely matches assay demand.

5 Claims, 9 Drawing Sheets

CLINICAL ANALYZER HAVING A VARIABLE CYCLE TIME AND THROUGHPUT

FIELD OF THE INVENTION

The present invention relates to a clinical analyzer having a method for increasing throughput. In particular, the present invention provides a clinical analyzer with a sampling arm automated in synchronization with a variable cycle time reaction cuvette transport in order to increase analyzer throughput.

BACKGROUND OF THE INVENTION

Various types of analytical tests related to patient diagnosis and therapy can be performed by analysis of a liquid sample taken from a patient's infections, bodily fluids or abscesses. These assays are typically conducted with automated clinical analyzers onto which tubes or vials containing patient samples have been loaded. The analyzer extracts liquid sample from the vial and combines the sample with various reagents in special reaction cuvettes or tubes. Usually the sample-reagent mixture is incubated or otherwise processed before being analyzed. Analytical measurements are often performed using a beam of interrogating radiation interacting with the sample-reagent mixture to generate turbidimetric, fluorometric, absorption readings or the like. The readings allow determination of end-point or rate values from which an amount of analyte related to the health of the patient may be determined using well-known calibration techniques.

There is incentive for increasing the efficiency of throughput of patient samples and one approach has been to vary the method for scheduling the operation of various assay devices on sample-reagent mixtures. Assay devices include aspiration probes for samples and reagents, mixing and washing stations, incubation and analytical stations, and the like. Reagent is usually initially dispensed into a reaction container or cuvette and sample is then added. The reagent-sample mixture is then transported from one assay device to another depending upon the assay being performed. The assay devices are operated under control of a computer having software programs used by those skilled in the art of computer-based electromechanical control programming to perform assays with related assay devices and assay operations given the identity of a patient sample, assay requests, and the like.

A number of different methods for controlling transportation between assay devices have been employed. One method operates all assay devices within a fixed cycle or length of time so that overall analyzer throughput is constant. Alternately, the assay devices may be controlled so that cycle times vary depending on the assay being conducted, a method known as "adaptive scheduling". The complexity of adaptive scheduling can adversely affect the throughput of the analyzer as the number of assay devices required for sophisticated assay increase. Various methods have been developed to improve both of these approaches.

U.S. Pat. No. 7,015,042 discloses a fixed-cycle process whereby incoming samples are partitioned into groups in accord with the length of time required for the assay to be completed or in accord with the pattern of reagent addition(s) taken with length of time required for the assay to be completed. Medium length time assays are completed, removed from a reaction carousel and replaced by shorter length time assays during a single operational cycle in which longer length assays are also completed.

U.S. Pat. No. 6,723,288 discloses a fixed cycle analyzer having an indexing drive for rotating a reaction carousel in a constant direction a predetermined numbers of incremental steps. The length of the circumference of carousel, the separation distance between reaction ports, the number of reaction ports and the number of increments per indexing are selected so that any given cuvette port returns to its original starting position after a fixed number of incremental steps. Throughput is determined by the fixed number of incremental steps multiplied by the sum of dwell time at each assay device and the time required for a stepwise movement.

U.S. Pat. No. 5,846,491 discloses an analyzer having a fixed cycle time for certain assay resources having a first fixed cycle time during which that assay resource is available to perform a predetermined operation on a sample-containing reaction vessel. Each of the other assay resources is also assigned a fixed cycle time, where the first cycle time is an integral multiple of the second cycle time, the two cycle times desirably being different from one another. As a result, control scheduling is simplified.

U.S. Pat. No. 5,576,215 discloses a process wherein the analyzer is operated in accordance with a schedule developed by a scheduler routine. The scheduler routine determines interval periods between operations performed by the analyzer on each biological sample as a function of an entered load list unless a fixed interval period between the operations is required and schedules instrument system operations and the determined interval periods. The analyzer assays the samples by operating its instrument systems in accordance with the developed schedule.

U.S. Pat. No. 5,252,612 discloses an analyzer that incrementally indexes a sample in a first direction in a set of increments wherein each increment represents a movement of the samples an amount corresponding to a number of samples. The movement of samples within all of the increments in the set of increments added together produces a sum which is a net move of the sample support an amount of samples equal to a second plurality of holders greater than one holder and less than the first plurality such that the greatest common factor between the second plurality and the first plurality is the number of increments in the set. Such a system enables separation of logical space from physical space in the system, allowing freedom in placement of assay devices while permitting proper sequencing of operations both in space and in time.

From the above descriptions of the art, it is apparent that, while throughput improvements have been made in controlling assay devices, the ability to quickly and efficiently operate an analyzer at different throughputs depending upon the assay load presented to the analyzer has not been achieved. In particular so-called "fixed cycle" analyzer can operate at only a single throughput, regardless of whether a larger number or a smaller number of assays need to be performed. Further, so-called "variable cycle" analyzers that rely on adaptive scheduling have a "variable throughput" but only as a consequence of the different types of assays to be performed, again, regardless of whether at larger number or a smaller number of assays need to be performed.

SUMMARY OF THE INVENTION

Assay load demand on a hospital or laboratory is subject to variation as a result of a number of factors including day of a week, time of a day, type of assays in the analyzer's menu, interfacing with a laboratory automation system and the like. This variation has a number of consequences on both operator personnel and analyzer operational capacity. There are inherent operational and consumable inefficiencies if an analyzer is capable of performing a relatively higher number of assays per hour, but if the assay load demand is a relatively lower number. It would be advantageous to be able to operate an analyzer at a throughput rate that most closely matches the assay demand load. The present invention meets this need by providing a clinical analyzer having the capability to operate at either of two different cycle times, depending upon the assay load demand experienced by the hospital or laboratory, so that analyzer throughput more closely matched assay demand. This ability to operate at either of two different cycle times is achieved by providing a sampling probe arm that can dispense patient sample into reaction containers or cuvettes at two different locations on a cuvette transport system. The sampling probe arm may be automatically extendable to reach the different circumferential locations or two different sampling probe arms may be interchangeably replaceable on the analyzer.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
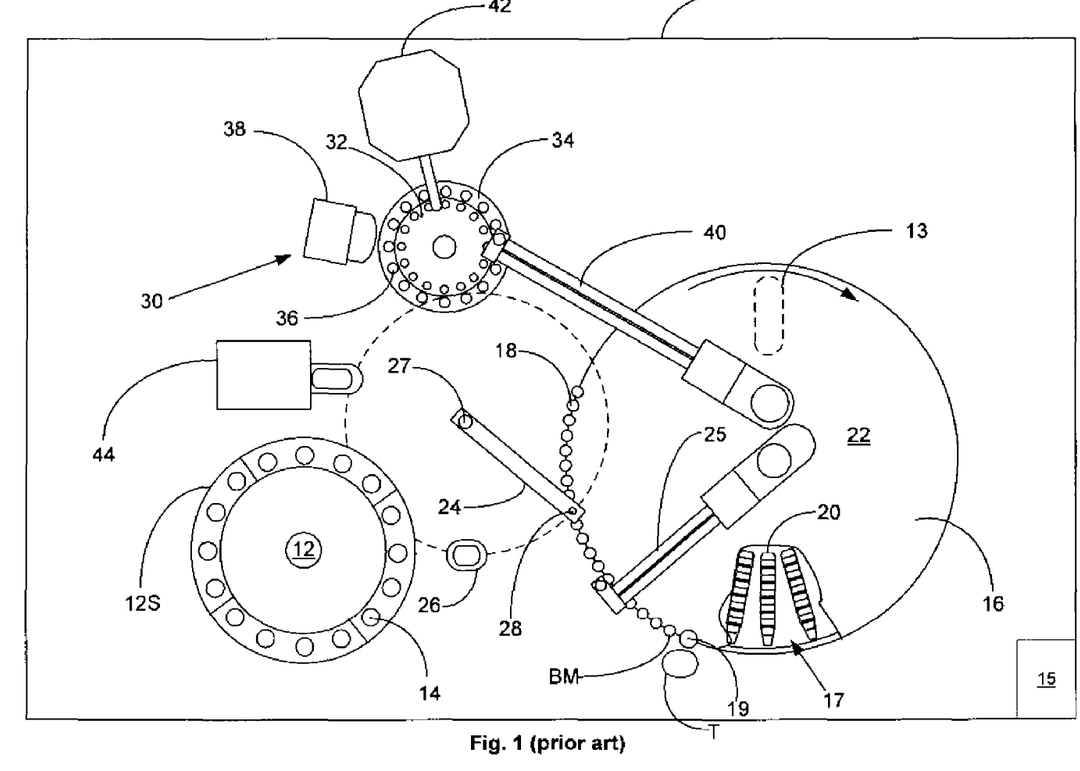
FIG. 1 is a schematic plan view of a prior art automated clinical analyzer in which the present invention may be advantageously employed.

The method and apparatus of this invention will be described initially with particular reference to FIG. 1 of the drawings. FIG. 1 shows schematically the elements of a conventional automatic chemical analyzer 10 comprising a patient sample carousel 12 supporting a plurality of sample tubes 14, a cuvette reaction carousel 16, adapted to hold a plurality of cuvettes 18, and a reagent carousel 17 for holding an inventory of reagents contained in a plurality of reagent cartridges 20, illustrated as disposed beneath a cut out portion of a lid 22, which covers various thermally controlled portions of cuvette carousel 16 and the reagent cartridges 20. Sample carousel 12 advantageously comprises a number of segmented sample tube carriers 12S, each adapted to hold a number of sample tubes 14. For convenience and compactness within analyzer 10, it is desirable to store all reagents needed to conduct a single assay within contiguous compartments or vessels. Typical of such reagent cartridges 20 is a multi-compartment or multi-well reagent cartridge 20 available for use in analyzer 10, sold by Dade Behring Inc., Deerfield, Ill. This multi-well reagent container 20 has the form of a container strip like described in U.S. Pat. No. 6,943,030, incorporated herein by reference, and includes a rigid peripheral band formed integrally with each of several reagent containing wells so that the container strip generally tapers in a substantially elongated wedge-like manner from a first edge to a second edge.

Cuvettes 18 may be formed, as described in U.S. Pat. No. 4,863,693, incorporated herein by reference, and as is done on the Dimension® clinical analyzer also sold by Siemens Medical Solutions Diagnostics, by pulling two different composition ribbons of clear film from a cuvette film cartridge, not shown, onto the periphery of the cuvette reaction carousel 16 at a molding station BM proximate a cuvette trashing station T. The cuvette reaction carousel 16 preferably has the form of a generally circular reaction cuvette transport system 16 capable of rotating in a plan around a central axis, and has about three hundred separate cavities 19 for holding cuvettes 18, the inner wall of each cavity having an opening to allow transmission of light through a cuvette 18 contained therein. A small opening remains at the top of each cuvette 18 to allow the addition of reagent liquid and sample liquid. A sample liquid arm 24 and a wash/drain 26 are located proximate the sample carousel 12 and cuvette carousel 16. Sample liquid arm 24 supports a conventional sample liquid probe 28 and is mounted to a rotatable shaft 27 so that movement of sample liquid arm 24 describes an arc intersecting the sample carousel 12, cuvettes 18, and the wash/drain 26. The wash/drain 26 may be used to clean the probe 28 as well as to drain unwanted fluids to a disposal.

A first reagent probe 25 is rotatably mounted above cuvette reaction carousel 16 and is adapted to draw reagent liquid from an appropriate reagent liquid cartridge 20 and to deposit reagent within a predetermined cuvette 18 for processing by the chemical analyzer 10. Probe 25 further comprises an ultrasonic mechanism used for aspirating, dispensing and mixing reagents. Since the hydrating, aspirating, dispensing and mixing mechanisms are well known in the art they need not be described further. An analytical photometric detector 13, shown in dashed lines, is located beneath the cuvette reaction carousel 16 and measures light absorbance through cuvettes 18 at various wavelengths, from which the presence of analyte in the sample liquid may be determined using well-known analytical techniques.

Analyzer 10 may also be equipped with a pre-assay sample processing module 30 like described in U.S. Pat. No. 5,985,672, incorporated herein by reference. The pre-assay sample processing module 30 facilitates the several additional steps necessary to perform heterogeneous assays without reducing the ability of analyzer 10 to maintain sample throughput. The processing module 30 permits processing either of or both of the sample liquid with analyte and/or the reagent liquid, before they are dispensed to a cuvette 18 for analytical reaction. Sample processing module 30 comprises an inner processing carousel 32 and an outer incubation carousel 34, housed in a thermal chamber, (not shown), the two carousels 32 and 34 being concentrically mounted with a common axis and preferably lying in a common plane, both preferably having a circular shape. Both carousels 32 and 34 are independently moveable and have a predetermined number of vessel holding means which may be clips, not shown, to support a plurality of individual pre-assay reaction vessels 36.

A second liquid probe 40 is rotatably mounted above cuvette carousel 16 and is adapted to draw reagent liquid from an appropriate reagent liquid cartridge 20 and deposit such reagent in a predetermined reaction vessel 36 in the incubation carousel 34. Sample liquid probe 40 is also adapted (1) to draw sample liquid from a reaction vessel 36 after the sample liquid has undergone the scheduled pre-assay operations and (2) to deposit sample liquid within a predetermined cuvette 18 for further processing and measurement.

Analyzer 10 is operated by computer-based controller 15 based on software written in a machine language, like that used on the Dimension® clinical chemistry analyzer sold by Siemens Medical Solutions Diagnostics, of Deerfield, Ill. and widely used by those skilled in the art of computer-based electromechanical control programming to perform assays and related operations given the identity of a patient sample, assay requests, and the like. Controller 15 is specifically programmed to rotate the cuvette reaction carousel 16 transport system at two different cycle times as well as to extend a sampling probe arm adapted for automatically dispensing sample into a reaction cuvette 18 carried by the cuvette reaction carousel 16, both as described hereinafter.

In the embodiment shown in FIG. 1, the analyzer 10 includes an analytical luminescence detector 42 adapted to detect luminescence of a reaction mixture in one of the reaction vessels 36. Preferably, detector 42 is a conventional luminometer or a chemiluminometer configured as a luminescent oxygen channeling immunoassays ("LOCI") reader, that is, the luminometer preferably is configured to allow the analyzer 10 to perform LOCI assays, like described in U.S. Pat. Nos. 5,340,716 and 5,709,994, both incorporated herein by reference. LOCI assays provide significant advantage over many conventional immunoassays run on automated analyzers because LOCI assays are highly specific and can be performed without many of the time-consuming separation steps typically associated with such conventional immunoassays. Furthermore, LOCI assays are a reliable method and results in less analyzer down time. As described previously, LOCI assays involve measurement of luminescence from a chemiluminescent compound which associates with a photosensitizer in the presence of a particular analyte. Optimally, the chemiluminescent compound is photochemically activated by singlet oxygen. The singlet oxygen is preferably produced by irradiating the photosensitizer. The light emitted by the chemiluminescent compound can be measured quantitatively to determine the amount of analyte. Accordingly, the reagents stored in cartridges 20 preferably include a photosensitizer and a complementary chemiluminescent compound. The detection unit 42 preferably is surrounded by an environmental chamber (not shown) which is adapted to shield detection unit 42 and the sample being analyzed from being exposed to environmental light, which would be detrimental to the assay. Furthermore, reaction vessels 36 and/or the accompanying cuvette reaction carousel 16 may be configured to shield light sensitive reagents or reaction mixture from surrounding environmental light.

In the embodiment shown in FIG. 1, the analyzer 10 also includes a conventional electrochemical measuring station 44 used to determine the concentration of specific ions and metabolites present in blood, plasma or serum, urine, and other biological fluids. Preferably, electrochemical measuring station 44 is configured as described in U.S. Pat. No. 5,964,994 incorporated herein by reference as an ion-selective-electrode (ISE) measuring station 44 and used to determine sodium and calcium ions as well as the pH, and carbon dioxide content in such fluids.

Figure 2:
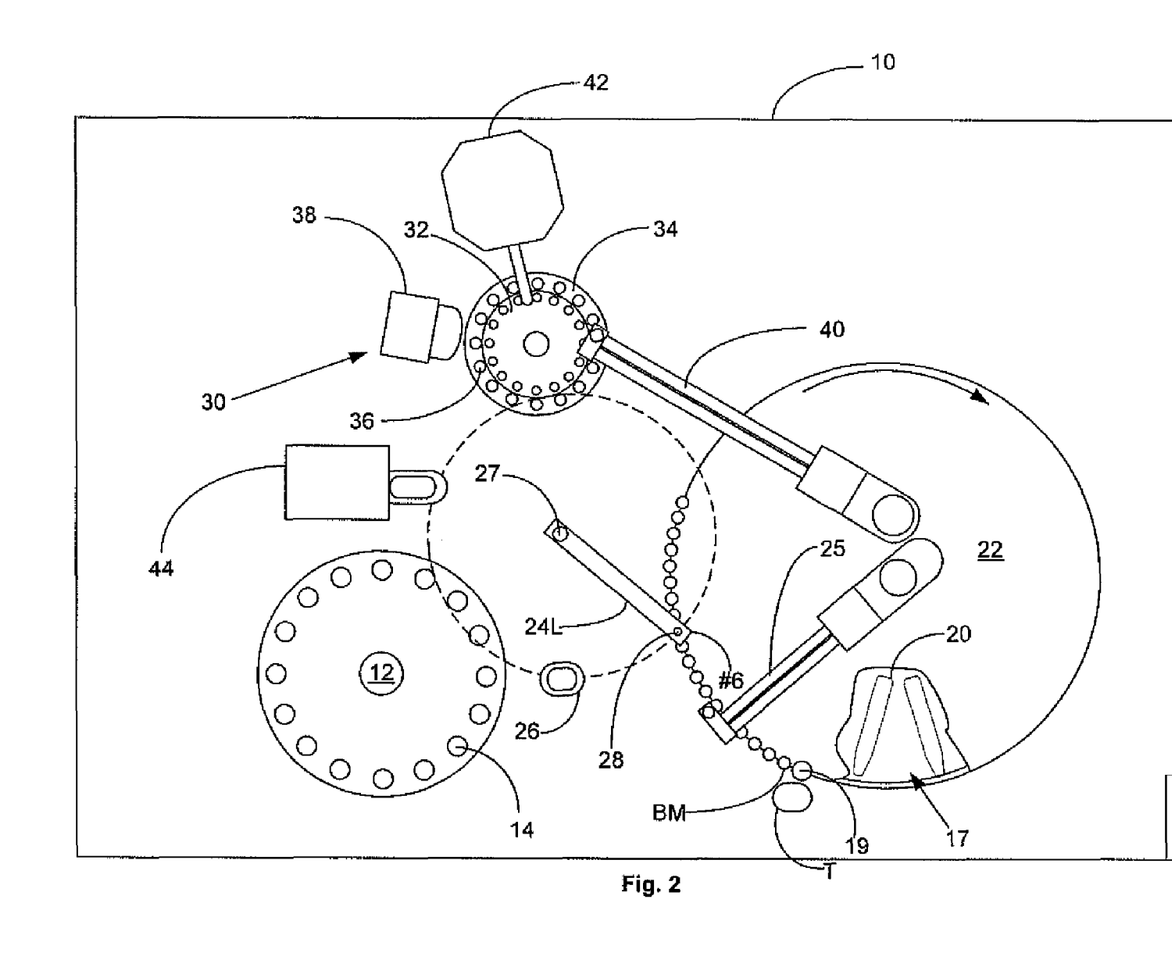
FIG. 2 is a schematic plan view of the clinical analyzer of FIG. 1, illustrating a first embodiment of a sampling probe adapted for dispensing sample into a reaction cuvette at a first location corresponding to a relatively smaller analyzer throughput.

FIG. 2 is a schematic plan view of the clinical analyzer of FIG. 1, illustrating a first embodiment of a "longer" sampling probe arm 24L adapted for dispensing sample from probe 28 into a reaction cuvette 18 at a first location indicated as #6 in order to achieve a relatively lower analyzer 10 throughput as a consequence of a relatively lower number of samples being presented to the analyzer for processing. In this embodiment, cuvette reaction carousel 16 is rotated clockwise, step-wise between next adjacent cavity 19 locations at a first illustrative "longer" cycle time of about 14.4 sec. between rotations. Sampling probe arm 24L is "longer" because a longer reach is required to dispense sample into a reaction cuvette 18 at location #6 in comparison to being able to dispense sample into a reaction cuvette 18 at a second location described hereinafter, indicated as #8 and corresponding to a relatively higher "cycle time" of about 7.2 seconds thereby increasing throughput of analyzer 10. This first illustrative cycle time is selected for producing a relatively lower analyzer throughput and is not restrictive for conducting the present invention. In the instance described above, cuvette reaction carousel 16 comprises three hundred (300) cavities 19 so that a total time of about 4,320 seconds (72 minutes or 1.2 hours) elapses between the time a cuvette 18 is formed at BM and the time that same cuvette 18 is disposed in trash T. As a consequence of these illustrative values, the assay throughput of analyzer 10 is about 250 assays/hour (300 cavities divided by 1.2 hours). As indicated in FIG. 2, sample is dispensed into a reaction cuvette 18 at a location #6, this location #6 being where a reaction cuvette 18 is located six (6) carousel rotational cycles (about 86 seconds) after that same reaction cuvette 18 is located beneath first reagent probe 25 and a first reagent R1 is dispensed thereinto.

Figure 3:
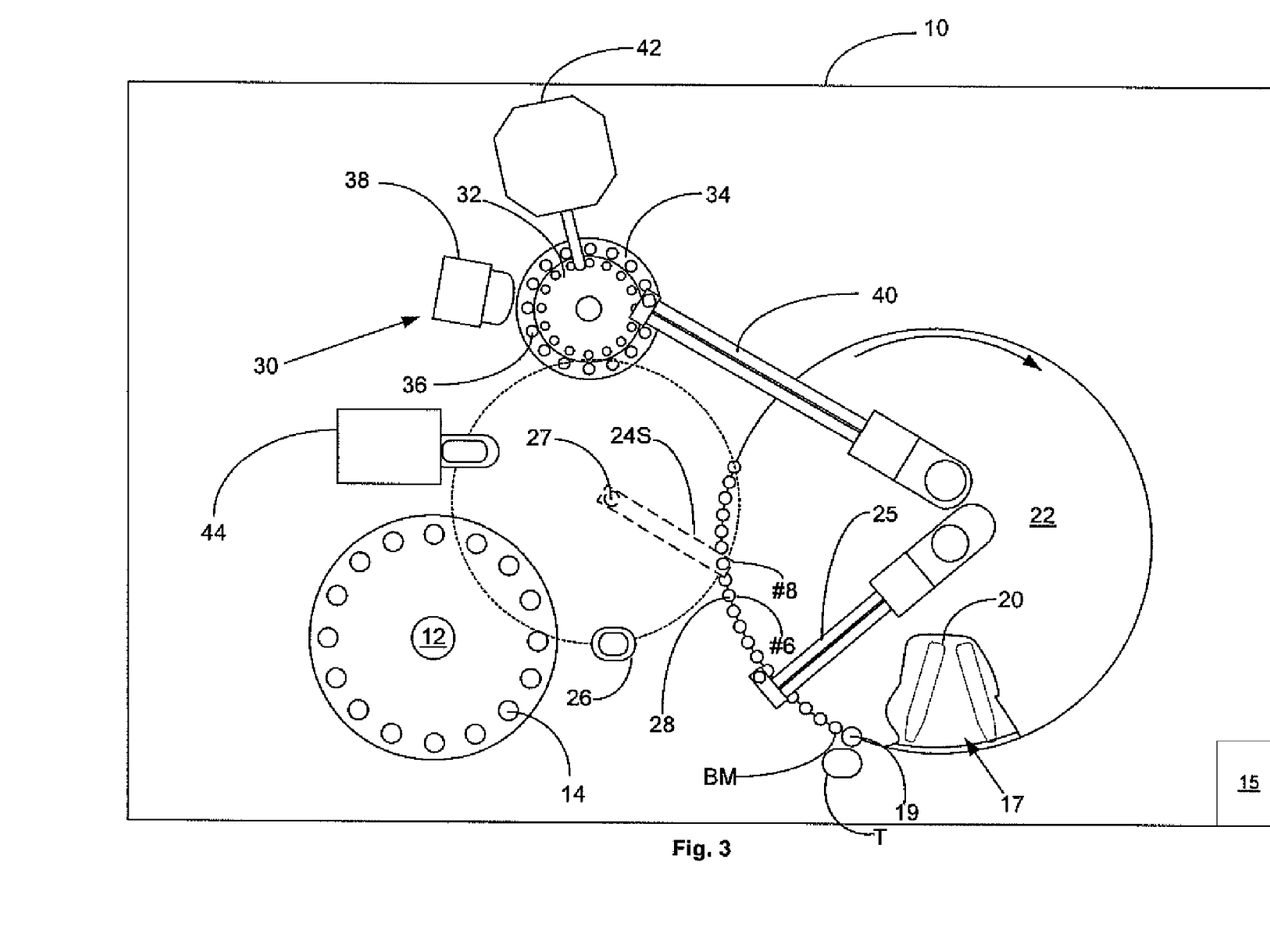
FIG. 3 is a schematic plan view of the clinical analyzer of FIG. 1, illustrating a second embodiment of a sampling probe adapted for dispensing sample into a reaction cuvette at a second location corresponding to a relatively larger analyzer throughput.

FIG. 3 is a schematic plan view of the clinical analyzer of FIG. 1, illustrating a second embodiment of sampling probe arm 24S adapted for dispensing sample from probe 28 into a reaction cuvette 18 at a second sample dispensing location indicated as #8 corresponding to a relatively higher analyzer 10 throughput. In this embodiment, cuvette reaction carousel 16 is rotated clockwise, step-wise between next adjacent cavity 19 locations at a second illustrative cycle time of about 7.2 sec. This second illustrative cycle time is selected for producing a relatively faster analyzer throughput and is not restrictive for conducting the present invention. As in the first instance, cuvette reaction carousel 16 comprises three hundred (300) cavities 19 so that a total time of about 2,160 seconds (36 minutes or 0.6 hours) elapses between the time a cuvette 18 is formed at BM and the time that same cuvette 18 is disposed in trash T. As a consequence of these illustrative values, the assay throughput of analyzer 10 is about 500 assays/hour (300 cavities divided by 0.6 hours). As indicated in FIG. 3, sample is dispensed into a reaction cuvette 18 at a location #8, this location #8 being where a reaction cuvette 18 is located eight (8) carousel rotational cycles (about 58 seconds) after that same reaction cuvette 18 is located beneath first reagent probe 25 and a first reagent R1 is dispensed thereinto.

Figure 4:
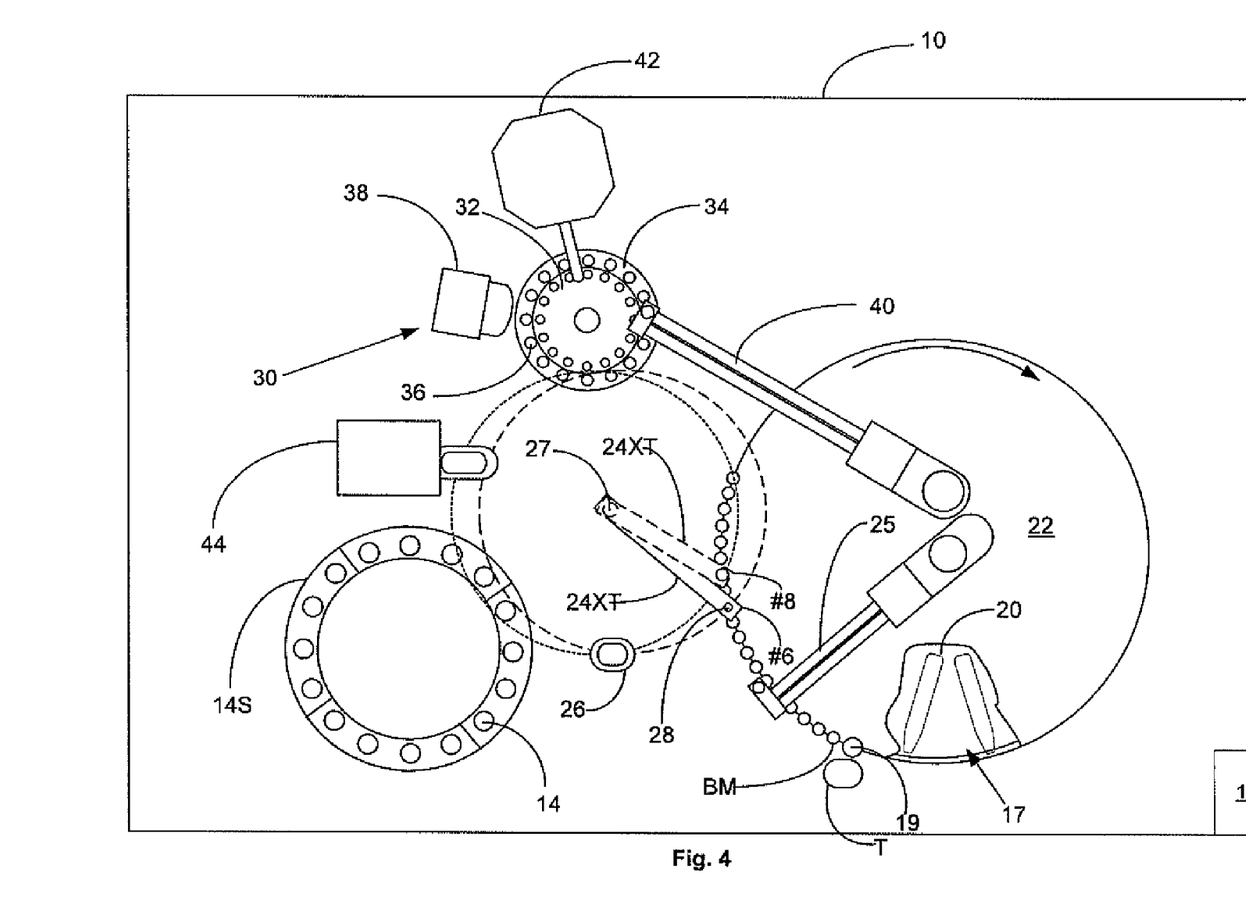
FIG. 4 is a schematic plan view of the clinical analyzer of FIG. 1, illustrating the sampling probe adapted for automatically dispensing sample into a reaction cuvette at either the first location of FIG. 2 or at the second location of FIG. 3.
Figure 5:
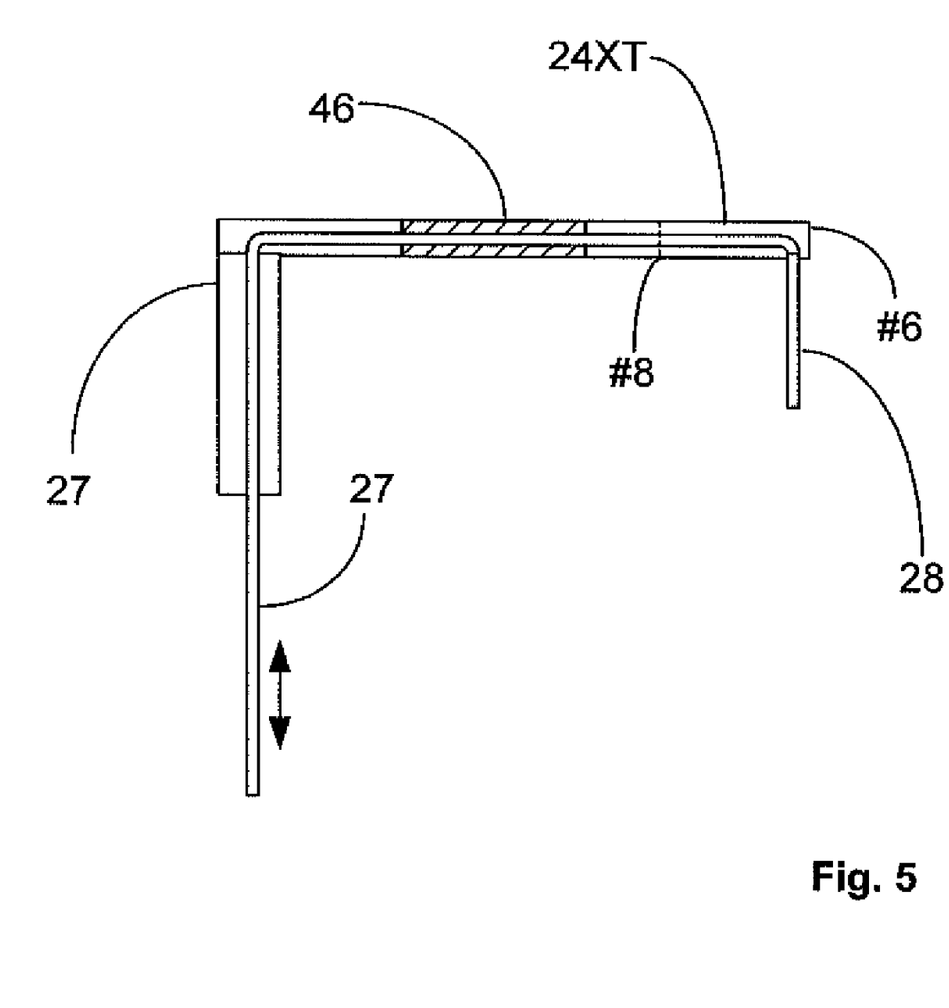
FIG. 5 is a simplified elevation schematic illustrating the extendable adaptation of the sampling probe of FIG. 4.

FIG. 4 is a schematic plan view of the clinical analyzer of FIG. 1, illustrating an extendible sampling probe arm 24XT adapted for automatically dispensing sample into a reaction cuvette 18 located at either the first sample dispensing location #6 of FIG. 2 or at the second sample dispensing location #8 of FIG. 3. In this instance, the extendible sampling probe arm 24XT is adapted to automatically assume the shorter length of sampling probe 24S or to automatically assume the length of longer sampling probe 24L, depending upon whether analyzer 10 is most efficiently operated at a higher or lower throughput. Sampling probe arm 24XT may be mechanically extended using for example an air-powered actuator portion 46 integral with sampling probe arm 24XT, in conjunction with the flexible nature of tubing 29 connecting probe 28 to a vacuum source, indicated by the double-headed arrow in FIG. 5). In such an instance, sampling probe arm 24XT can be adjusted in length to reach sampling locations 36 and #8, by being made longer, respectively. Alternately, sampling probe arm 24S and sampling probe arm 24L may be made to be mechanically interchangeable with minor adjustments to the probe 28 access input locations of wash/drain 26 and electrochemical measuring station 44. The present invention thereby provides a simple and inexpensive method for essentially doubling the throughput of analyzer 10, for example from about 250 assays/hour to about 500 assays/hour, using the illustrative parameters listed above for number of cavities 19 and cycle times.

Figure 9:
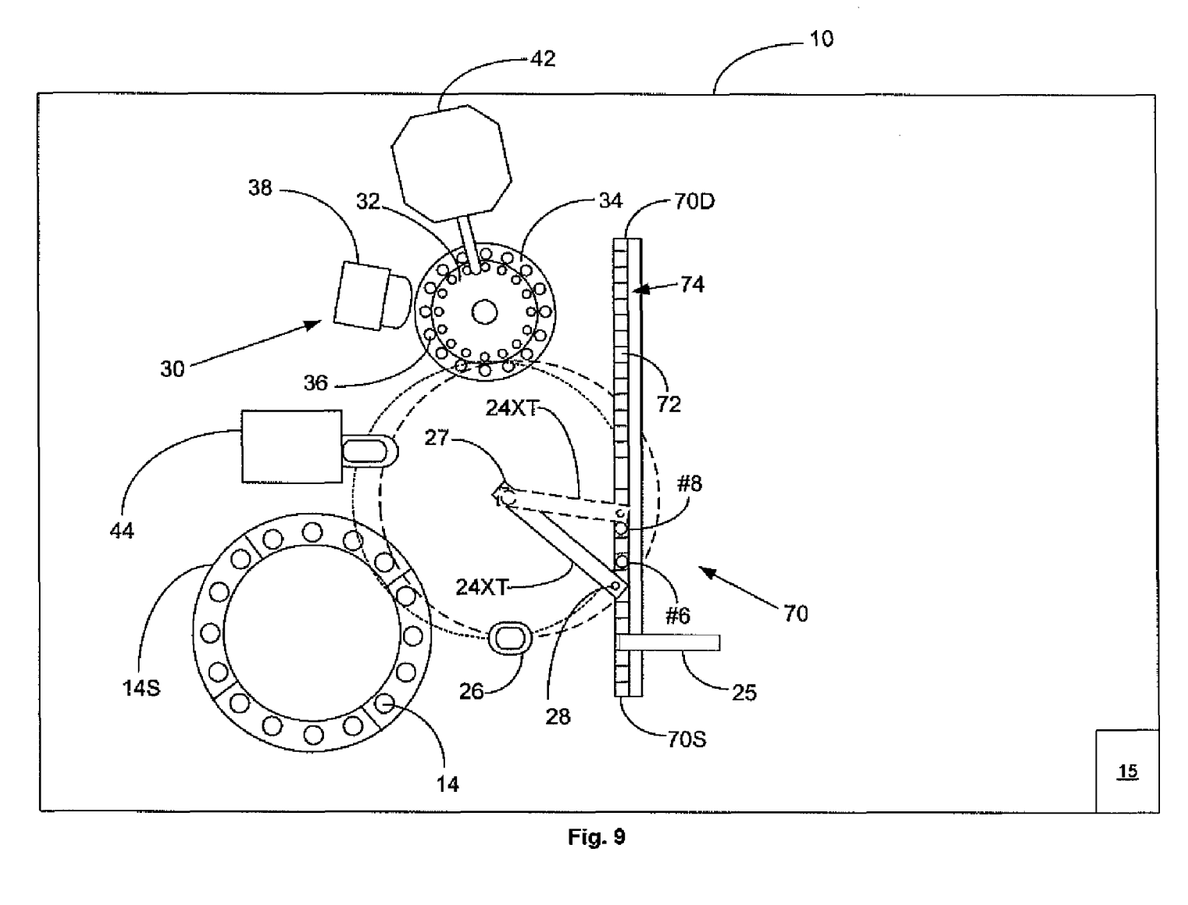

For example, reaction carousel 16 can have the form of an "endless" chain-like transport system 70 like illustrated in FIG. 9 with reaction cuvettes 18 held in stepwise moveable slots 72 in a flexible belt 74 wherein samples to be assayed are contained in cuvettes 18 entering chain-like transport system 70 at a supply end 70S and analyzed samples being disposed at an opposed disposal end 70D end. In such a chain-like transport system 70, empty slots 72 are typically moved from the disposal end 70D to the supply end 70S by doubling over flexible belt 74 extendible sampling probe arm 24XT adapted for automatically dispensing sample into a reaction cuvette 18 located at either the first sample dispensing location #6 or at the second sample dispensing location #8 beyond reagent probe 25. Again, the extendible sampling probe arm 24XT is adapted to automatically assume the shorter length of sampling probe 24S or to automatically assume the length of longer sampling probe 24L, depending upon whether analyzer 10 is most efficiently operated at a higher or lower throughput. Alternately, the "endless chain" transport system 70 may have a generally circuitous geometry in a plane and passing by various assay devices like reagent probe 25 disposed proximate transport system 70.

Figure 6:
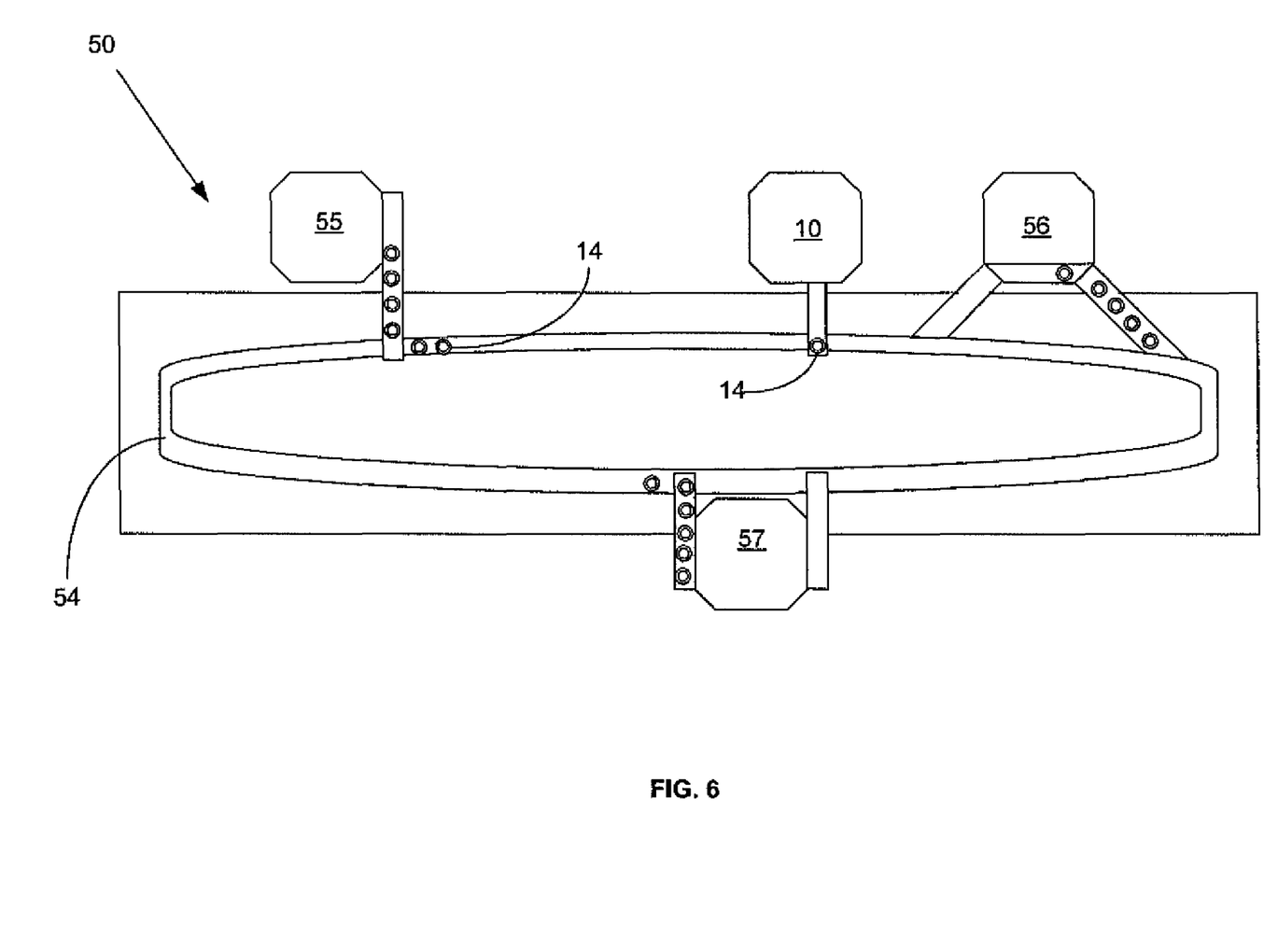
FIG. 6 is a schematic plan view of the clinical analyzer of FIG. 3 operated in conjunction with a Laboratory Automation System.

An additional environment in which the present invention may be advantageously used involves the instance in which a number of analytical devices are "linked together" by an Laboratory Automation System (LAS), such as those described in U.S. Pat. Nos. 6,984,527 and 6,442,440, both incorporated herein by reference, which have been recently developed to handle a number of different patient specimens (blood, urine, and body fluids) contained in standard, bar code-labeled, evacuated tubes 14. The bar code label contains an accession number coupled to demographic information that is entered into a hospital's Laboratory Information System (LIS) together with test orders and other desired information. An operator places the labeled tubes onto the LAS system which performs all functions automatically including sample sorting, routing, centrifugation, aliquot preparation, sample analysis at one or more analyzers, including analyzer 10, before making the tested sample available for post-analytical storage and retrieval. Typical of such LAS 50, very simplified in FIG. 6, a sample tube 14 is transported proximate analyzer 10 being carried in a tube carrier 52 and transported by a primary conveyor 54 and either removed from the primary conveyor by a robotic-like device and placed into a sampling area of analyzer 10; alternately, using a robotic-like probe and pipette, sample aliquots may be removed from the sample while it remains on the primary conveyor and subsequently transferred to another of usually several other analytical devices, indicated as 55, 56 and 57. Depending upon the tests to be conducted on sample in tubes 14 and the menu of the different analytical devices, a large number of samples may be scheduled to be performed in analytical devices 55, 56 and 57, other than analyzer 10, while a small number of assays may be scheduled to be performed on analyzer 10. Such a situation is depicted in FIG. 6, where a relatively larger number of samples 14 are illustrated for analytical devices 55, 56 and 57. Again, for reasons of economy, it would be desirable to be able to operate analyzer at a relatively lower throughput, and as described above, this may be achieved using the sampling probe arm 24L and a longer cycle time as shown in FIG. 2.

Figure 7:
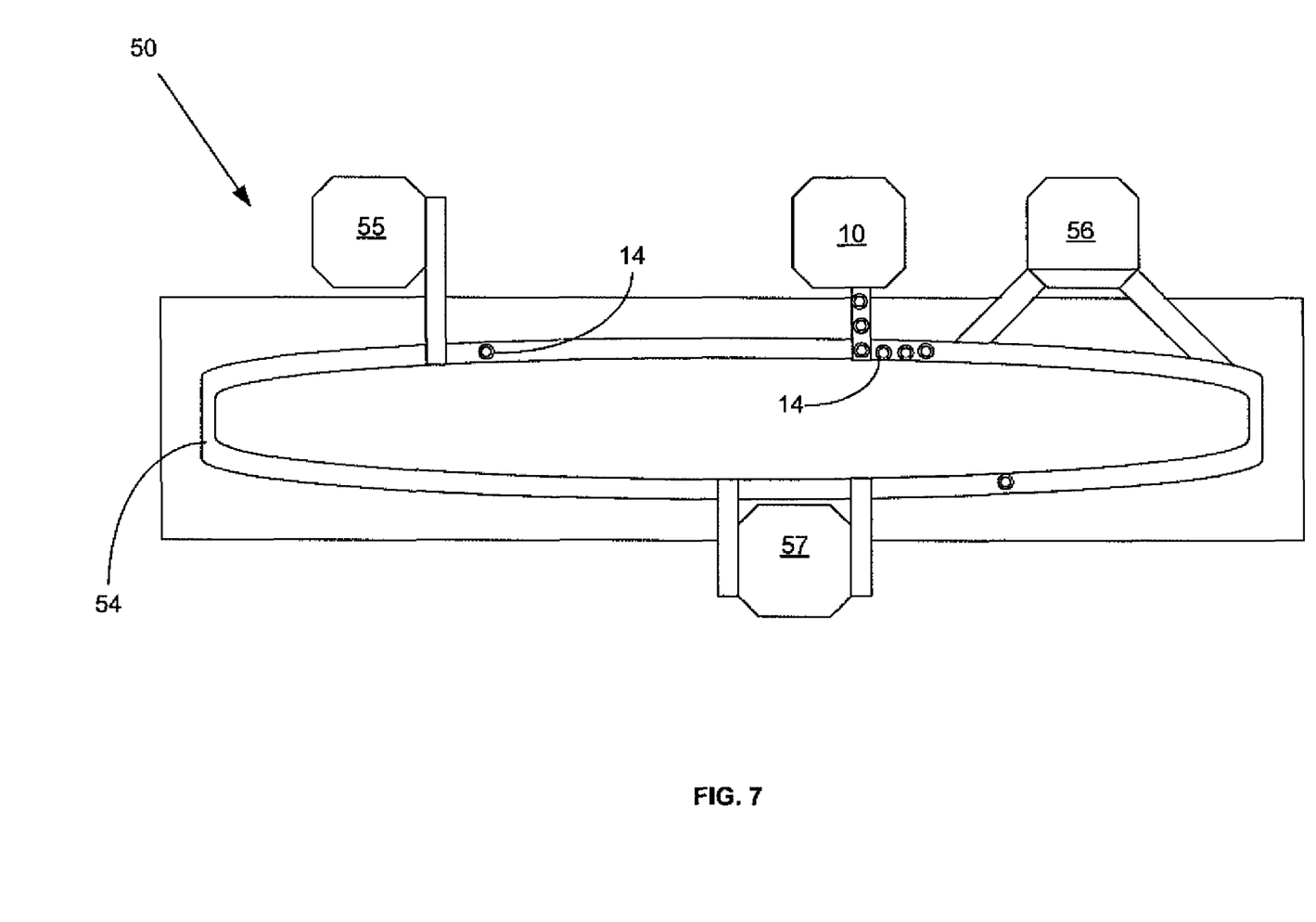
FIG. 7 is a schematic plan view of the clinical analyzer of FIG. 3 operated in conjunction with a Laboratory Automation System in the instance that a relatively large number of samples are to analyzed the analyzer of FIG. 3; and, FIG. 8 is a schematic plan view of the clinical analyzer of FIG. 3 operated in conjunction with a reagent supply system equipped for automatically adding reagents that will be needed by the analyzer of FIG. 3 to conduct future scheduled assays; and, FIG. 9 is a schematic plan view of the clinical analyzer of FIG. 3 operated in an embodiment having an alternate transport system.

Conversely, the tests to be conducted on sample in tubes 14 may dictate that a larger number of samples are scheduled to be performed in analyzer 10 as opposed to a small number of assays scheduled to be performed in analytical devices 55, 56 and 57. Such a situation is depicted in FIG. 7, where a relatively smaller number of samples 14 are illustrated for analytical devices 55, 56 and 57 and a relatively larger number of samples 14 are to analyzed by analyzer 10. In this instance, for reasons of processing efficiency, it would be desirable to be able to operate analyzer 10 at a relatively higher throughput, and as described above, this may be achieved using the sampling probe arm 24S and a shorter cycle time as shown in FIG. 3.

In those situations wherein analyzer 10 is operated at the relatively higher throughput provided by sampling probe arm 24S and a shorter cycle time, the consumption of reagents contained in reagent cartridges 20 also proceeds at a higher rate than when analyzer 20 is operated at a relatively lower throughput. A key factor in maintaining an optimum assay throughput within analyzer 10 is the ability to timely resupply reagent containers 20 into reagent carousel 17 before the reagents contained therein become exhausted so that an uninterrupted supply of reagent cartridges 20 is available when analyzer 10 is operated at higher throughput rates. This challenge may be met by programming computer 15 to track reagent and assay consumption along with time, and date of consumption of all reagents consumed out of each reagent container 20 on a per reagent container and per assay basis for specifically defined time periods. Using this consumption data, time, and current reagent container 20 inventory of already on-board reagents within reagent carousel 17, computer 15 may be programmed to make an inventory demand analysis for specifically defined future time periods. This analysis determines future assay inventory needs for specifically defined time periods and can be displayed or issued as a list of all of the reagent containers 20 that need to be supplied to analyzer 10 in a timely manner prior to the actual need of every reagent container 20.

Figure 8:
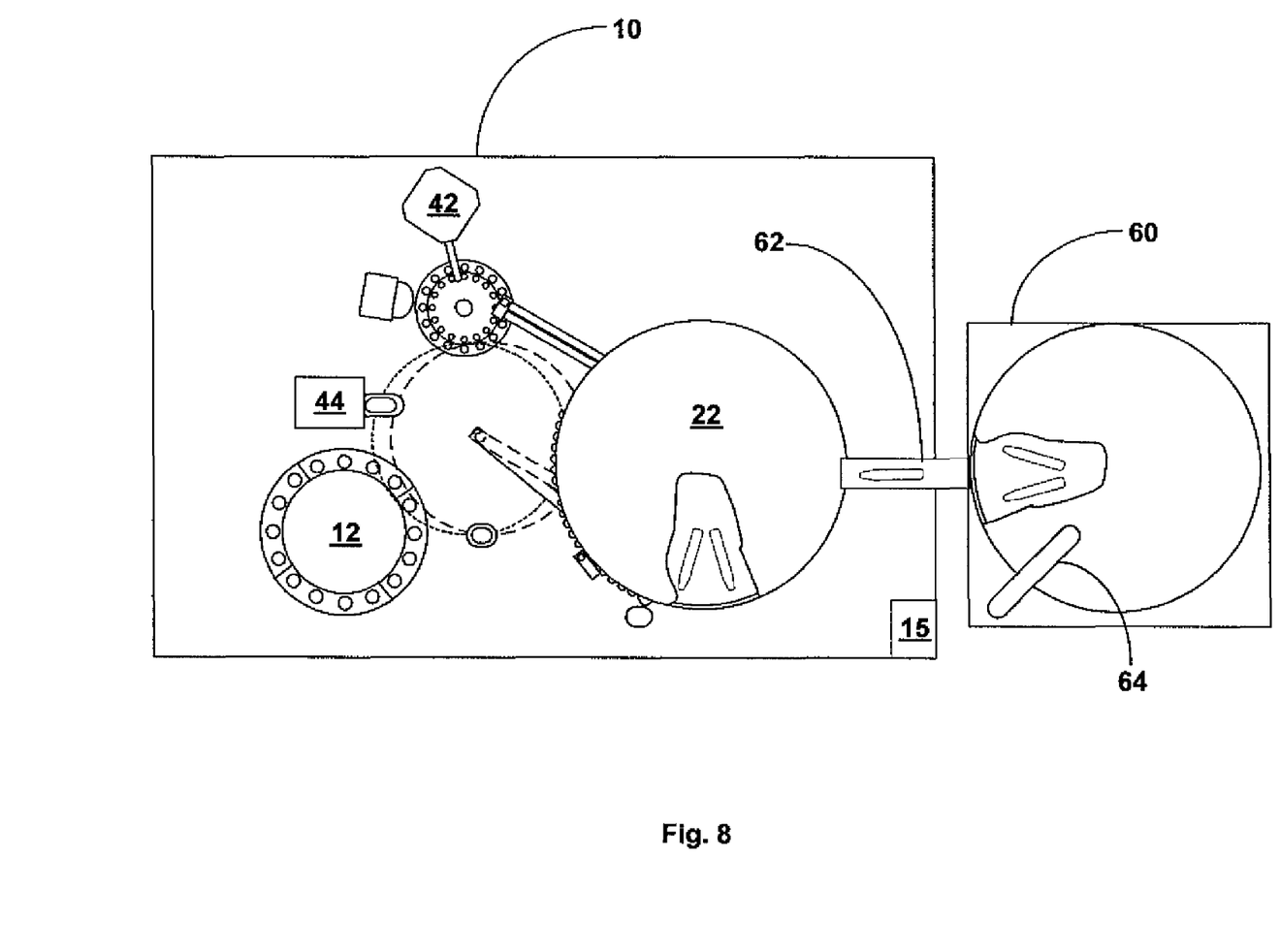

To achieve this objective and to simultaneously minimize operator involvement, it is advantageous that analyzer 10 be mated with an automated reagent supply system 60 into which reagent containers 20 that will be needed in the near future may be placed, these future needed reagent containers having been identified by an analysis like the one described above. Reagent supply system 60 is equipped with a bi-directional shuttle 62 for automatically removing reagent cartridges 20 having the regents therein exhausted from analyzer 10 and automatically adding reagent cartridges 20 that will be needed by analyzer 10 to conduct future scheduled assays into reagent carousel 17 (FIG. 8). To provide useful stability to certain reagents between manufacture and use in an assay, it is sometimes necessary to lyophilize one or more reagents into a tablet form prior to being placed in reagent container 20. Consequently, reagent supply system 60 is advantageously equipped with a combined re-hydration and ultrasonic mixing station 64 for re-hydrating and uniformly mixing the tablets into a liquid reagent prior to a reagent container 20 being shuttled onto analyzer 10. Reagent supply system 60 may also be operated by controller 15 in order to supply requisite reagent cartridges 20 as described above, thereby maintaining an uninterrupted inventory of requisite reagent cartridges 17 within analyzer 10 when analyzer 10 is operating at a higher throughput level, like associated with FIG. 3.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A clinical analyzer having the capability to operate at either of two different assay throughputs, said analyzer comprising:
   a carousel supporting a plurality of sample tubes;
   a reaction cuvette transport system capable of transporting sample aspirated from said sample tubes to a number of assay devices;
   a controller programmed to move the reaction cuvette transport system at first and second cycle times, the first and second cycle times characterized by having either a shorter dwell time or a longer dwell time between rotations of the cuvette transport system, respectively; and
   a sampling probe arm mechanically extendible between a shorter arm length when the reaction cuvette transport system is moved at the first cycle time having the shorter dwell time and a longer arm length when the reaction cuvette transport system is moved at the second cycle time having the longer dwell time so that the sampling probe arm is capable of dispensing sample aspirated from said sample tubes into reaction cuvettes carried by said cuvette transport system at two different locations on the cuvette transport system.

2. The clinical analyzer of claim 1, wherein the shorter and longer dwell times differ by about a multiple factor of two (2).

3. The clinical analyzer of claim 1 further comprising a Laboratory Automation System (LAS) comprising a tube carrier transported by a conveyor, and a pipettor for removing sample aliquots from a liquid sample within said LAS and transferring the sample aliquot to a sample carousel within said analyzer.

4. The clinical analyzer of claim 1 further comprising a reagent inventory carousel and an automated reagent supply system adapted for automatically removing reagent cartridges from the reagent carousel and for automatically adding reagent cartridges into the reagent carousel.

5. The clinical analyzer of claim 1 further comprising a photometric detector, a luminescence detector, and an electrochemical measuring station.

* * * * *